United States Patent [19]

Buckanin

[11] Patent Number: 5,380,778
[45] Date of Patent: Jan. 10, 1995

[54] FLUOROCHEMICAL AMINOALCOHOLS

[75] Inventor: Richard S. Buckanin, Woodbury, Minn.

[73] Assignee: Minnesota Mining and Manufacturing Company, St. Paul, Minn.

[21] Appl. No.: 954,336

[22] Filed: Sep. 30, 1992

[51] Int. Cl.$^6$ .............................................. C08K 5/17
[52] U.S. Cl. .................... 524/247; 524/167; 524/168; 524/241; 428/364
[58] Field of Search ................ 524/167, 168, 241, 247

[56] References Cited

U.S. PATENT DOCUMENTS

| | | | |
|---|---|---|---|
| 2,399,118 | 4/1946 | Homeyer | 260/307 |
| 2,437,388 | 3/1948 | Homeyer | 260/307 |
| 2,759,019 | 8/1956 | Brown et al. | 260/556 |
| 2,802,002 | 8/1957 | Gever | 260/240 |
| 3,644,513 | 2/1972 | Sweeney | 524/217 |
| 3,824,126 | 7/1974 | Katsushima et al. | 524/217 |
| 3,870,748 | 3/1975 | Katsushima et al. | 260/475 F |
| 3,899,563 | 8/1975 | Oxenrider et al. | 264/211 |
| 4,084,059 | 4/1978 | Katsushima et al. | 560/87 |
| 4,266,080 | 5/1981 | Falk et al. | 568/45 |
| 4,468,527 | 8/1984 | Patel | 564/96 |
| 4,789,491 | 12/1988 | Chang et al. | 252/8.75 |
| 4,806,255 | 2/1989 | Konig et al. | 252/8.75 |
| 4,833,188 | 5/1989 | Kortmann et al. | 252/8.8 |
| 4,840,738 | 6/1989 | Hardy et al. | 252/8.8 |
| 4,877,540 | 10/1989 | Engelhardt et al. | 252/8.8 |
| 4,900,455 | 2/1990 | Kolbe et al. | 252/8.8 |
| 4,925,577 | 5/1990 | Borcher, Sr. et al. | 252/8.8 |
| 4,958,039 | 9/1990 | Pechhold | 252/8.8 |
| 5,025,052 | 6/1991 | Crater et al. | 524/104 |
| 5,079,076 | 1/1992 | Lal | 252/8.75 |

FOREIGN PATENT DOCUMENTS

| | | |
|---|---|---|
| 1604039 | 6/1971 | France . |
| 2018448 | 1/1987 | Japan ................................... 524/217 |
| 9218569 | 10/1992 | WIPO . |
| WO93/07914 | 4/1993 | WIPO . |

OTHER PUBLICATIONS

Banks, Ed., Organofluorine Chemicals and Their Industrial Applications, Ellis Horwood Ltd., Chichester England, 1979, pp. 226–234.

Mares, F., et al., "Modification of Fiber Surfaces by Monomeric Additives, Part I: Extrusion Techniques," Textile Research Journal, vol. 47, No. 8, pp. 551–561.

Mares, F., et al., "Modification of Fiber Surfaces by Monomeric Additives, Part II: Absorption of Fluorocarbon Additives by Polyethylene Terephthalate," Textile Research Journal, vol. 48, No. 4, pp. 3218–3229.

H. Plenkiewicz and W. Dmowski, in "Synthetic Utility of 3-(Perfluoro-1,1-Dimethylbutyl)-1-Propene. Part II. Synthesis of New 2-Hydroxy-3-(Perfluoroalkyl)-Propyl-Amines", Journal of Fluorine Chemistry, vol. 45, pp. 389–400 (1989).

*Primary Examiner*—Kriellion S. Morgan
*Attorney, Agent, or Firm*—Gary L. Griswold; Walter N. Kirn; Robert H. Brink

[57] ABSTRACT

Mixture of fluorochemical and thermoplastic polymer are disclosed. Such fluorochemicals are fluorochemical alcohols and fluorochemical oxazolidinone compositions. The fluorochemicals inpart oil and water repellency to the surfaces of shaped articles made from the mixtures.

10 Claims, No Drawings

FLUOROCHEMICAL AMINOALCOHOLS

This invention relates to the use of fluorochemical compositions to impart water and oil repellency to shaped articles, such as fibers and films. In another aspect it relates to fluorochemical aminoalcohols, their preparation, and their use. In another aspect it relates to fluorochemical oxazolidinone compositions, their preparation, and their use. In a still further aspect it relates to thermoplastic mixtures comprising a fluorochemical and a thermoplastic polymer, such as polypropylene, and to the shaped articles thereof, such as fibers and films.

The use of various fluoroaliphatic radical-containing substances, e.g. Scotchgard TM carpet protector on fibers and fibrous substrates, such as textiles, paper, and leather, to impart oil and water repellency, is known. See, for example, Banks, Ed., *Organofluorine Chemicals and Their Industrial Applications*, Ellis Horwood Ltd., Chichester England, 1979, pp. 226–234. Such fluoroaliphatic radical-containing substances include, for example, fluoroaliphatic-containing alcohols (U.S. Pat. No. 4,468,527, Patel), fluoroaliphatic radical-containing amines (U.S. Pat. No. 2,759,019, Brown et al.), and fluoroaliphatic radical-containing oxazolidinones U.S. Pat. No. 5,025,052, Crater et al.).

Certain fluoroaliphatic radical-containing aminoalcohols have been disclosed in U.S. Pat. Nos. 3,870,748 (Katsushima, et. al.) and 4,084,059 (Katsushima, et. al.), which describe the use of certain fluoroaliphatic radical-containing aminoalcohols in solutions or emulsions for the treatment of fabrics and fibers. Certain fluoroaliphatic radical-containing aminoalcohols have also been disclosed by H. Plenkiewicz and W. Dmowski, in "Synthetic Utility of 3-(Perfluoro-1,1-Dimethylbutyl)-1-Propene. Part II. Synthesis of New 2-Hydroxy-3-(Perfluoroalkyl)Propyl-Amines", *Journal of Fluorine Chemistry*, Vol. 45, pp. 389–400 (1989). Plenkiewicz and Dmowski prepared several fluoroaliphatic-containing aminoalcohols by treatment of the corresponding fluoroaliphatic radical-containing epoxide with ammonia or aliphatic or cycloaliphatic amines.

Various fluoroaliphatic radical-containing compositions can be applied to various fibrous substrates, such as carpet, by methods which include, for example, spraying, padding, and finish bath immersion. Certain fluoroaliphatic radical-containing compositions may be used as melt additives by melt extrusion of a blend of a synthetic organic fiber-forming polymer and a fluoroaliphatic radical-containing composition. Such melt extrusion is described, for example, by Mares, F., et al., "Modification of Fiber Surfaces by Monomeric Additives, Part I: Extrusion Techniques" *Textile Research Journal*, Vol. 47, No. 8, pp. 551–61 and Mares, F., et al., "Modification of Fiber Surfaces by Monomeric Additives, Part II: Absorption of Fluorocarbon Additives by Polyethylene Terephthalate", *Textile Research Journal*, Vol. 48, No. 4, pp. 3218–29, and in U.S. Pat. No. 3,899,563 (Oxenrider et al.).

U.S. Pat. No. 5,025,052 (Crater et al.) discloses certain fluoroaliphatic radical-containing oxazolidinone compositions used as melt additives to prepare fibers and films exhibiting low surface energy. The Crater et al. patent discloses several methods for preparation of fluoroaliphatic radical-containing oxazolidones from organic isocyanate or urethane precursors.

Hydrocarbon, that is, fluorine-free, oxazolidinones have been prepared by the treatment of aminoalcohols with dialkylcarbonates. U.S. Pat. Nos. 2,437,388 (Homeyer), 2,399,118 (Homeyer), and 2,802,002 (Gever).

Briefly, in one aspect, the present invention provides a thermoplastic composition comprising fluoroaliphatic radical-containing aminoalcohol and thermoplastic synthetic organic polymer, such as polyamide, polyurethane, polyester, and polyolefin, e.g. polypropylene. The thermoplastic composition can be melted and shaped, for example by extrusion or molding, to produce shaped articles, such as fibers and films. Said fluoroaliphatic radical-containing aminoalcohol imparts desirable oil- and water-repellencies to the surfaces of said shaped articles.

Fluoroaliphatic radical-containing aminoalcohols (some of which are novel) useful in the present invention comprise a fluoroaliphatic moiety and an aminoalcohol moiety. A class of said aminoalcohols are those in which said aminoalcohol moiety includes a secondary aliphatic hydroxyl group and a primary, secondary, or tertiary aliphatic-amino group. The amino group and the hydroxyl group are each bonded to different aliphatic, fully-saturated carbon atoms, which are bonded to each other on a hydrocarbon chain. The hydroxyl group is located on the hydrocarbon chain proximal to the fluoroaliphatic moiety, and the amino group is located distal to the fluoroaliphatic moiety. The fluoroaliphatic moiety comprises at least two, preferably three, fully-fluorinated, saturated aliphatic carbon atoms which are preferably in a chain that can be straight (normal) chain or branched chain, e.g., $-(CF_2)_3-$ or $-CF(CF_3)CF_2-$, or cyclic or part of a cyclic chain. At the melting or processing temperature of the polymer, said fluoroaliphatic radical-containing aminoalcohols preferably are meltable, non-volatile, compatible with the thermoplastic polymer, and non-reactive with the thermoplastic polymer.

This invention also provides a method for preparation of fluoroaliphatic radical-containing oxazolidinone compositions by reacting fluoroaliphatic radical-containing aminoalcohol with dialkyl carbonate, without the use of organic isocyanates or urethanes. The fluoroaliphatic radical-containing oxazolidinone compositions of the present invention are prepared by reacting the above-described fluoroaliphatic radical-containing aminoalcohol, where said amino group is primary or secondary, with a disubstituted carbonate, such as dimethylcarbonate or diphenylcarbonate.

This invention also provides a mixture comprising a fluoroaliphatic radical-containing oxazolidinone composition prepared by the method of the present invention and a thermoplastic synthetic organic polymer, such as polyamide, polyurethane, polyester, and polyolefin, e.g. polypropylene. The thermoplastic composition can be melted and shaped, for example by extrusion or molding, to produce shaped articles, such as fibers and films. Said fluoroaliphatic radical-containing oxazolidinone imparts desirable oil and water repellencies to the surfaces of said shaped articles.

This invention also provides shaped articles such as pellets, fibers, and films prepared, for example, by melt extrusion, and molded articles prepared, for example, by injection molding the mixtures of the present invention. These shaped articles comprise thermoplastic synthetic organic polymer and fluoroaliphatic radical-containing aminoalcohol, or fluoroaliphatic radical-containing oxazolidinone composition prepared by the method of this invention, or both. The resulting pellets, fibers, films, etc. have low surface-energy surfaces which results in oil- and warepellency and anti-soiling properties.

A class of the fluoroaliphatic radical-containing aminoalcohols useful in this invention can be represented by Formula I.

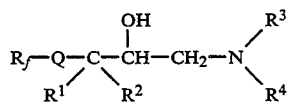

I thereof. $R^3$ and $R^4$ can contain hetero atoms and can, together with the nitrogen atom to which they are bonded, form a heterocyclic ring of 5 to 8 carbon atoms, such as piperazine, pyrrolidine, morpholine, and pyrrole. Particularly preferred aminoalcohols are those in which $R^3$ or $R^4$ comprises a saturated hydrocarbon of formula $C_yH_{2y+1}$ where y is from 4 to 20.

$R^3$ or $R^4$ can also be sufficiently complex so that Formula I represents a molecule containing more than one aminoalcohol moiety. These molecules can be represented by Formula II.

In Formula II, each $R^3$ is independently as described above for Formula I.

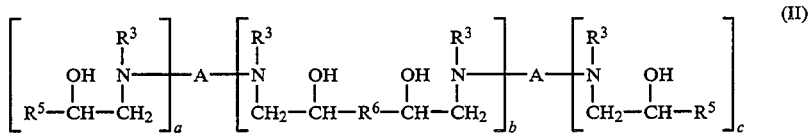

(II)

In Formula I, $R_f$ is a fluoroaliphatic group or radical which is a fluorinated, monovalent, saturated aliphatic radical of at least two, preferably at least five, fully-fluorinated carbon atoms. It can be straight chain, branched chain, or, if sufficiently large, cyclic, or combinations thereof, such as alkylcycloaliphatic radicals. The skeletal chain in the fluoroaliphatic group can include catenary oxygen, hexavalent sulfur, and/or trivalent nitrogen hetero atoms bonded only to carbon atoms of the skeletal chain, such hetero atoms providing stable linkages between fluorocarbon portions of the $R_f$ group. While $R_f$ can have a large number of carbon atoms, compounds where $R_f$ has up to 20 carbon atoms will be adequate and preferred since large $R_f$ groups usually represent a less efficient utilization of fluorine than is possible with smaller $R_f$ groups. Generally $R_f$ will have 3 to 20 carbon atoms, preferably 6 to about 12, and will contain 40 to 78 weight percent, preferably 50 to 78 weight percent, fluorine. The terminal portion of the $R_f$ group is a perfluorinated moiety which will preferably contain at least 7 fluorine atoms, e.g., $CF_3CF_2CF_2$—, $(CF_3)_2CF$—, $F_5SCF_2$—, or the like. The preferred group is fully or substantially completely fluorinated, as in the case
- 6 where $R_f$ is perfluoroalkyl, e.g. $CF_3(CF_2)_2$-. $R_f$ may have up to 20 carbon atoms and include, for example, $C_8F_{17}$—, $C_6F_{13}CH_2CH_2$—, $C_{10}F_{21}CH_2CH_2$—.

The divalent linking group Q in Formula I provides a means to link $R_f$ with the depicted organic moiety containing the hydroxyl and amino groups. Q can comprise a hetero atom-containing group, e.g., a group containing, —S—, —O—, and/or —N(R)—, or an organic group or a combination of such groups, examples of which are aliphatic, e.g., -(CH$_2$)$_n$—where n is 0 to 6 (note that Q is a covalent bond when n is 0), aromatic, oxy, thio, carbonyl, sulfone, sulfoxy, —N(CH$_3$)—, sulfonamide, carbonamido, sulfonamidoalkylene, e.g., —SO$_2$NR(CH$_2$)$_e$, where e is 1 to 6 and R is lower alkyl having 1 to 4 carbon atoms, carbonamidoalkylene, and carbonyloxy.

In Formula I, $R^1$ and $R^2$ are independently H or lower alkyl of 1 to 6 carbon atoms, or $R^1$ and $R^2$ can, together with the carbon atom to which they are bonded, form a cyclic aliphatic ring of 5 to 8 carbon atoms.

In Formula I, $R^3$ and $R^4$ are independently H, aryl, aliphatic, cycloaliphatic radical, or combinations In Formula II, a is 0 or 1, b is a whole number from 0 to about 6, and c is 0 or 1. The sum of a+b+c is at least 1 and there is at least one fluoroaliphatic radical-containing aminoalcohol moiety as defined by Formula I.

In Formula II, each $R^5$ is independently H or an organic radical and can be selected from alkyl, cycloalkyl, aryl, and combinations thereof, e.g., aralkyl, and can contain halogen atoms, fluoroaliphatic radicals, $R_f$, and one or more hetero atoms or hetero atom-containing moieties, e.g. 0, S, SO, SO$_2$, N, and CO. At least one $R^5$ is $R_f$—Q—C($R^1$)($R^2$)— where $R_f$, $R^1R^2$, and Q are as defined above for Formula I. Suitable $R^5$ groups can have up to 20 carbons and include, for example, H—, ClCH$_2$—, C$_6$H$_5$—, C$_6$H$_5$OCH$_2$—, C$_8$F$_{17}$SO$_2$N(CH$_3$)CH$_2$—, C$_6$F$_{13}$—$CH_2$OCH$_2$—, and C$_{10}$F$_{21}$CH$_2$CH$_2$SCH$_2$CH$_2$OCH$_2$—.

In Formula II, $R^6$ is a divalent organic linking group which can be selected from alkylene groups such as ethylene, propylene, hexylene, and methylene dicyclohexylene, having 2 to about 20 carbon atoms, aralkylene groups, such as -CH$_2$C$_6$H$_4$CH$_2$—and —C$_6$H$_4$CH$_2$C$_6$H$_4$—, having up to 20 carbon atoms, arylene groups, such as tolylene and various combinations of these groups. The $R_6$ groups can also contain $R_f$ radicals and one or more hetero atoms or hetero atom-containing moieties, e.g., O, S, SO, SO$_2$, N, and CO. Suitable $R^6$ groups include, for example, —CH$_2$O(CH$_2$)$_4$OCH$_2$—, —CH$_2$OCOC$_6$H$_4$COOCH$_2$—, —CH$_2$OC$_6$H$_4$C(CH$_3$)$_2$C$_6$H$_4$ OCH$_2$—, C$_8$F$_{17}$SO$_2$N(CH$_2$—)$_2$, C$_6$F$_{13}$CON$_9$CH$_2$—.

The organic linking group A in Formula II is a mono-, di- or polyvalent organic radical, such as alkyl (e.g. butyl, hexyl ), aryl (e.g. phenyl), aralkyl (e.g. tolyl), alkylene (e.g. ethylene, hexamethylene), arylene, (e.g., tolylene), or aralkylene (e.g., —CH$_2$C$_6$H$_4$CH$_2$— and —C$_6$H$_4$CH$_2$C$_6$H$_4$—). The organic linking groups can have up to 20 carbon atoms and can contain one or more of the hetero atoms or hetero atom-containing moieties, e.g., O, S, SO, SO$_2$, N, and CO. The A group can be the residue of an organic amine from which aminoalcohol moieties are formed. That is, A is the residue of an organic amine exclusive of the amino functional group.

In each of the above fluoroaliphatic radical-containing aminoalcohols of general Formula II, where there are a plurality of $R^5$, $R^6$, and A groups or moieties, each can be the same or different. Also, Formula II represents individual compounds or mixtures of compounds, for example, as they are obtained as products from reactions used in their preparation. In addition, small amounts of by-products, with and without the fluoroaliphatic radical $R_f$ and not represented by Formula II, can also be present in small amounts in said mixtures or reaction products because of the reaction conditions involved in their preparation. The presence of such small amounts of by-products, generally less than 10 weight percent of the mixture, does not effect the usefulness of the fluoroaliphatic radical-containing aminoalcohol mixtures or compounds of this invention.

Representative fluoroaliphatic radical-containing aminoalcohols useful in the present invention include:

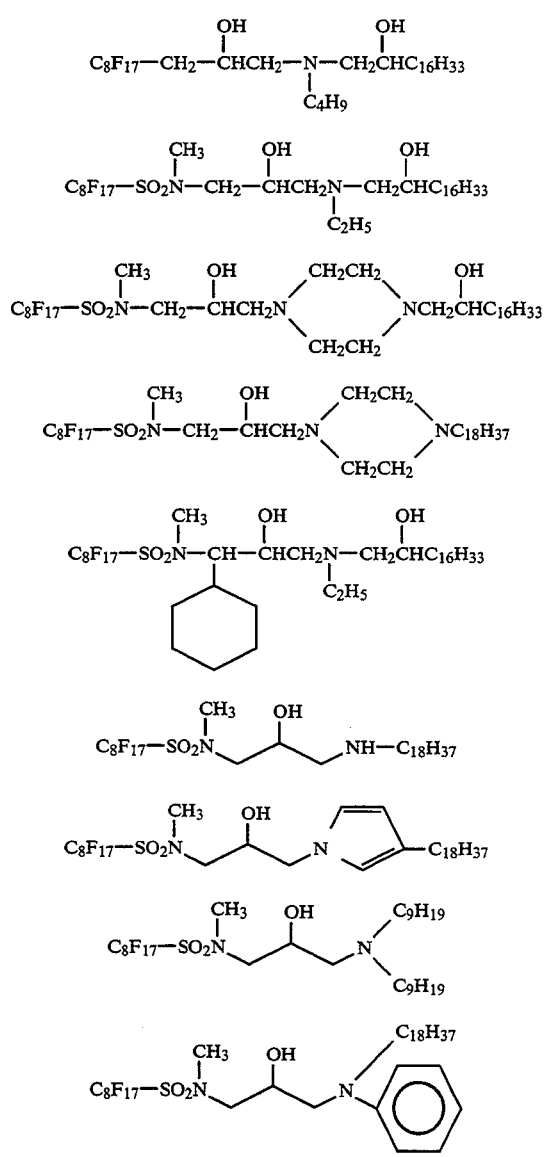

A novel subclass of the fluoroaliphatic radical-containing aminoalcohols represented by Formula I are those where $R_f$, $R^1$, $R^2$, $R^3$, and $R^4$ are as described above and where Q is an oxygen containing moiety selected from the group consisting of —CO—, —CONR—13 $SO_3NR$—, —$SO_2$—, or combinations thereof, where R is H or lower alkyl containing 1 to 6 carbon atoms.

The fluoroaliphatic radical-containing aminoalcohols can be prepared using known organic reactions, such as those disclosed in the Katsushima, et. al. patents, supra, and by H. Plenkiewicz and W. Dmowski, supra. In each of these patents and publication the preferred method of preparation is by the reaction of fluoroaliphatic radical-containing epoxides with amines. Representative reaction schemes for the preparation of fluoroaliphatic radical-containing aminoalcohols are outlined below in Schemes A, B and C where $R_f$, Q, $R^1$, $R^2$, $R^3$, and $R^4$ are as described above.

The fluoroaliphatic radical-containing aminoalcohols can also be prepared by the displacement

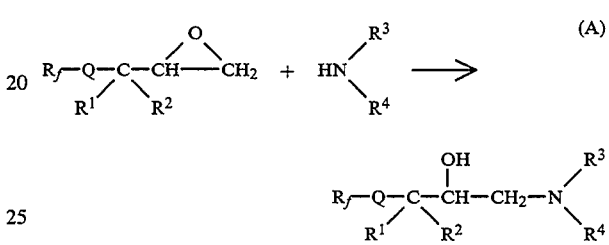

of a leaving group from the corresponding fluoroaliphatic radical-containing alcohol. Where X is a leaving group such as halogen or tosyl.

The fluoroaliphatic radical-containing aminoalcohols may also be prepared by hydrolysis of the

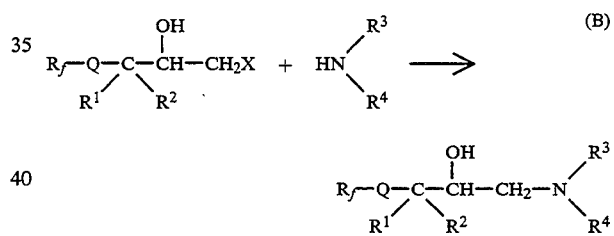

corresponding oxazolidinone.

Fluoroaliphatic radical-containing

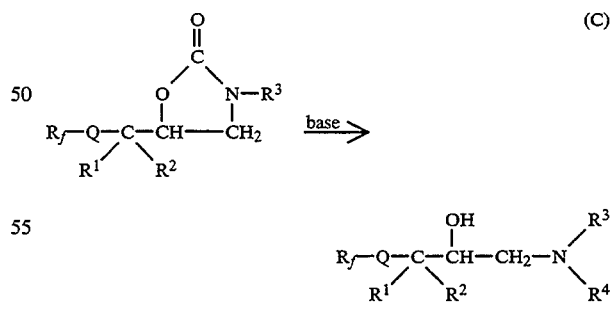

aminoalcohols in which the amino group is primary or secondary can be treated with dialkyl carbonates to give fluoroaliphatic radical-containing oxazolidinones. A representative reaction scheme for the preparation of fluoroaliphatic radical-containing oxazolidinones is outlined below in Scheme D where $R_f$, Q, $R^1$, $R^2$, $R^3$, and $R^4$ are as described above.

Generally, the fluoroaliphatic

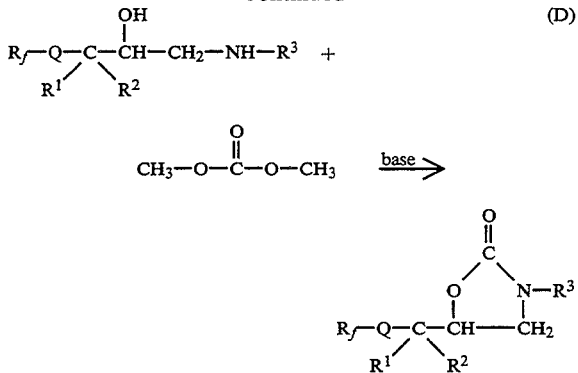

radical-containing aminoalcohols and the fluoroaliphatic radical-containing oxazolidinone compositions (the two classes hereinafter collectively called fluoroaliphatic radical-containing compositions) useful in this invention will contain about 20 to 70 weight percent, preferably about 25 to 50 weight percent, of carbon-bonded fluorine. If the fluorine content is less than about 20 weight percent, an impractically large amount of the fluoroaliphatic-containing composition will generally be required to impart desired oil- and water-repellencies to the surfaces of resulting shaped articles, while fluorine contents greater than about 70 weight percent are unnecessary to achieve the desired surface properties and thus represent an uneconomical use of fluorine.

The fluoroaliphatic radical-containing compositions are particularly useful as additives in melts of synthetic organic thermoplastic polymers to impart desired oil and water repellencies to the surfaces of resulting shaped articles. Such polymers include synthetic linear polyamide, e.g., nylon-6 and nylon-66, polyester, e.g., polyethylene terephthalate, polyurethane, and polyolefin, e.g., polyethylene and polypropylene.

The shaped articles, e.g., fibers and films, of this invention can be made, e.g., by blending or otherwise uniformly mixing the normally solid fluoroaliphatic radical-containing composition with the solid synthetic polymer, for example by intimately mixing the solid fluoroaliphatic radical-containing composition with pelletized or powdered polymer, and melt extruding the mixture into shaped articles such as pellets, fibers, or films by known methods. The fluoroaliphatic radical-containing composition can be mixed per se with the polymer or the fluoroaliphatic radical-containing composition can be mixed with the polymer in the form of a "masterbatch" (concentrate) of the fluoroaliphatic radical-containing composition in the polymer. Masterbatches typically contain from about 10% to about 25% by weight of the Fluoroaliphatic radical-containing composition. Also, an organic solution of the fluoroaliphatic radical-containing composition may be mixed with the powdered or pelletized polymer, the mixture dried to remove solvent, then melted and extruded into the desired shaped article. Alternatively, molten fluoroaliphatic radical-containing composition (as a compound(s) or masterbatch) can be injected into a molten polymer stream to form a blend just prior to extrusion into the desired shaped article.

In addition to their use in modifying the properties of fibers, e.g., polypropylene carpet fibers, as described above, the fluoroaliphatic radical-containing compositions are also useful as blend additives to thermoplastic polymer melts from which blown microfibers are made for use in making non-woven fabrics having low surface energy, oil and water repellency, or soiling resistance.

The amount of fluoroaliphatic radical-containing composition used as additive to polymer melts is that amount sufficient to produce a shaped article having a surface with the desired properties of oil and water repellency, or soiling resistance. Preferably, the amount of fluoroaliphatic radical-containing composition to be used will be that amount which provides from about 100 to 10,000 ppm fluorine, more preferably 200 to 5000 ppm, most preferably 400 to 3000 ppm fluorine, based on the weight of the shaped article.

After melt extrusion of fiber or film, an annealing step may be carried out to enhance oil and water repellency. This annealing process can be conducted below the melt temperature of the synthetic polymer, for example, in the case of nylon, at about 150° to 220° C. for a period of about 30 seconds to 5 minutes. In some cases, the presence of moisture during annealing, e.g., by using an autoclave to anneal, can improve the effectiveness of the fluoroaliphatic radical-containing composition.

The following nonlimiting examples are presented to further describe and illustrate the invention.

EXAMPLES

Various fluoroaliphatic radical-containing compositions were prepared, mixed with thermoplastic polymer, and extruded into fiber. The resulting fiber was knitted into tubular socks or texturized into carpet samples. The oil- and water-repellency of the socks and carpet samples, and the walk-on soiling-resistance of the carpet samples was evaluated.

Water Repellency (WR) Test

The water repellency of socks and carpet samples was measured using a water-isopropyl alcohol test, and is expressed in terms of a water-repellency rating of the carpet or sock. Samples which were resistant only to 100 percent water, i.e. not penetrated by, (0 percent isopropyl alcohol) the least penetrating of the test mixtures, were given a rating of 0, (representing the amount of isopropyl alcohol present) whereas samples resistant to 100 percent isopropyl alcohol, the most penetrating of the test mixtures were given a rating of 10. Other intermediate values are determined by use of other water-isopropyl alcohol mixtures. The water-repellency rating corresponds to the most penetrating mixture which does not penetrate or wet the sample after 10 seconds contact. If not even resistant to 100% water, the sample was given a rating of F. In general a water repellency rating of 1 (90% water/10% isopropyl alcohol) or better, e.g., 2 (80% water/20% isopropyl alcohol) is desirable for carpet.

Oil Repellency (OR) Test

The oil repellency of socks and carpet samples was measured by AATCC Standard Test 118-1978, which test is based on the resistance of samples to penetration by oils of varying surface tensions. Samples resistant only to Nujol TM mineral oil, the least penetrating of the test oils, are given a rating of 1, whereas treated fabrics resistant to heptane (the most penetrating of the test oils) are given a value of 8. If not even resistant to Nujol TM mineral oil, the sample was given a rating of F. Other intermediate values are determined by use of other pure oils or mixtures of oils. The rated oil-repellency corresponds to the most penetrating oil (or mixture of oils) which does not penetrate or wet the sample after 10 seconds contact rather than the 30 seconds contact of the Standard Test. Higher numbers indicate better oil-repellency. In general, an oil repellency of 2 or greater is desirable.

Walk-On-Soiling (WOS) Test

The soil resistance of carpet was determined by exposure to pedestrian traffic according to AATCC Test method 122-1979. The exposure site was the corridor (hallway) in a heavily travelled industrial building for an exposure of about 30,000 "traffics" for each one WOS cycle. The samples were repositioned periodically to insure uniform exposure and were vacuumed every 24 hours. After each WOS exposure cycle, i e 30,000 "traffics" and before visual evaluation, the carpet samples were vacuumed then subjected to steam cleaning using a Mr. Clean TM carpet steam cleaning machine employing an aqueous cleaning solution prepared from a solution of 4 ounces of STEAMEX TM carpet cleaner in 1 gallon of 49° C. water, passing the machine over the carpet squares first in one direction then once at right angles. The samples were rinsed, using tap water in the steam cleaning machine, then allowed to dry overnight and visually evaluated for degree of soiling as compared to an untreated carpet sample. After rating, additional soiling cycles and ratings were generally done on each carpet sample, including in each case a WOS cycle, vacuuming, steam cleaning, drying and visual rating. Rating values vary from $-6$ to $+6$ as described, minus ($-$) values indicating greater soiling than the control, and positive ($+$) values indicating less soiling than the control, and 0 indicating the same soiling as the control.

| WOS Rating* | Description |
|---|---|
| 0 | equal to control |
| $-$ or $+$ 2 | slightly better ($+$) or worse ($-$) than control |
| $-$ or $+$ 4 | significant difference compared to control |
| $-$ or $+$ 6 | very significant difference compared to control |

*Grey scale values multiplied by 4

Fluorine Content

The fluorine content of each fiber was measured by burn analysis after extrusion.

Preparation of Socks

Fluoroaliphatic radical-containing compounds were dry mixed with 12 melt-flow index polypropylene resin pellets in the amount shown in Table 5 and extruded as 13.2 denier filaments using a 1.25 inch diameter single screw extruder. The extruder temperatures were 225° C. (zone 1), 230° C. (zone 2), 240° C. (zone 3), and 245° C. (zone 4). The fibers were knit into tubular socks having a circumference of about 17.8 cm using a 10th gauge tubular knitter (Carolina Labknit) from Speizman Industries. The socks were then annealed at a temperature of 135° C. and a relative humidity of 100% for 2 minutes.

Preparation of Carpet Samples

Fluoroaliphatic radical-containing compounds were dry mixed with 12 melt-flow polypropylene resin pellets in the amount shown in Table 6 and extruded as 13.2 denier filaments using a 1.25 inch diameter single screw extruder. The extruder temperatures were 225° C. (zone 1), 230° C. (zone 2), 240° C. (zone 3), and 245° C. (zone 4). The fibers were texturized using a Hills air-jet draw-texturizing machine and tufted on a 30.5 cm sample tufter. The carpet samples were then annealed at a temperature of 135° C. and a relative humidity of 100% for 2 minutes.

Example 1

N-methyl-N-glycidyl-perfluorooctanesulfonamide ("epoxide A") was prepared by placing 450 grams N-methyl-perfluorooctanesulfonamide ("amide A") in a two-liter three-necked round-bottom flask and heating to 80° C. 101 grams epichlorohydrin was then added followed by 91 grams methanol. The temperature was reduced to 65° C. before 30 grams 25 wt % sodium methoxide in methanol solution was slowly added keeping the temperature below 70° C. 60 grams 50 wt % aqueous sodium hydroxide solution was slowly added keeping the temperature below 70° C. After addition the reaction was stirred at 65° C. overnight. Water-aspirator vacuum was applied to the flask and excess methanol and epichlorohydrin were removed. 450 grams water was then added to the flask with stirring at 65° to wash the product. The water was decanted after allowing the product to settle. This washing step was repeated a second time. Vacuum was applied to 20 mm Hg and the temperature of the flask was raised to 90° C. to remove volatile materials.

In a one-liter, three-necked round bottom flask fitted with a mechanical stirrer, condenser, gas inlet tube, thermometer, and electric heating mantel were placed 250.0 g (0.44 moles) of epoxide A and 250 mL toluene solvent under a nitrogen blanket. To this stirred solution heated to 60° C. was added 118.4 g (0.44 moles) octadecylamine in small portions over a 15 minute period. After addition of the amine was complete the temperature of the reaction was raised to 115° and the reaction was stirred for 12 hours at this temperature until all of the starting epoxide had been converted to aminoalcohol as determined by gas chromatographic analysis. The reaction mixture was cooled to a temperature of about 25° C. and excess toluene solvent was removed under vacuum with a rotary evaporator. Infrared, proton NMR, and mass spectroscopic analysis confirmed the product to be a fluorochemical aminoalcohol of this invention having the structure $C_8F_{17}$-$SO_2N(CH_3)CH_2$-$CH(OH)CH_2NH$-$C_{18}H_{37}$.

EXAMPLES 2–8

Additional aminoalcohols of this invention were prepared as in Example 1 by reacting the appropriately substituted amine (butyl, hexyl, dodecyl or octadecyl amine) with the corresponding epoxides of structure

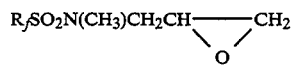

with varying $R_f$ chain lengths to give fluorochemical aminoalcohols of this invention having the structure $R_fSO_2N(CH_3)CH_2$-$CH(OH)CH_2NH$-$R_H$, where $R_f$ and $R_H$ were as shown in Table 1.

N-ethyl-perfluorbutanesulfonamide ($C_4F_9SO_2N(H)CH_2CH_3$) was prepared by placing 302 grams perfluorobutanesulfonyl fluoride and 500 mL diisopropyl ether in a two liter three-necked round bottom flask under nitrogen. Next 139.5 grams ethylamine (3.1 equivalents) was slowly added while keeping the temperature below 60° C. After addition was complete the reaction mixture was stirred at 60° C. overnight. Next, 500 milliliters of 6 M sulfuric acid was added. The organic layer was isolated and washed two times with equal volumes of water. The solvent was removed under reduced pressure the give the sulfonamide. The sulfonamides with varying $R_f$ were prepared using this procedure but with the appropriate perfluoroalkanesulfonyl fluoride. The corresponding epoxides were prepared from these sulfonamides in the same manner as described in example 1.

TABLE 1

Structures of Examples 1-8
$R_f\text{SO}_2\text{N}(\text{CH}_3)\text{CH}_2\text{—CH(OH)CH}_2\text{NH-}R_H$

| Example | $R_f$ | $R_H$ |
| --- | --- | --- |
| 1 | $C_8F_{17}$ | $C_{18}F_{37}$ |
| 2 | $C_8F_{17}$ | $C_4H_9$ |
| 3 | $C_8F_{17}$ | $C_{12}H_{25}$ |
| 4 | $C_8F_{17}$ | $C_6H_{13}$ |
| 5 | $C_6F_{13}$ | $C_4H_9$ |
| 6 | $C_6F_{13}$ | $C_{18}H_{37}$ |
| 7 | $C_{10}F_{21}$ | $C_4H_9$ |
| 8 | $C_{10}F_{21}$ | $C_{18}H_{37}$ |

Examples 9-11

Additional aminoalcohols of this invention were prepared by reacting either hexyl or octadecyl amine with the appropriate epoxide

TABLE 1

Structures of Examples 1-8
$R_f\text{SO}_2\text{N}(\text{CH}_3)\text{CH}_2\text{—CH(OH)CH}_2\text{NH-}R_H$

| Example | $R_f$ | $R_H$ |
| --- | --- | --- |
| 1 | $C_8F_{17}$ | $C_{18}F_{37}$ |
| 2 | $C_8F_{17}$ | $C_4H_9$ |
| 3 | $C_8F_{17}$ | $C_{12}H_{25}$ |
| 4 | $C_8F_{17}$ | $C_6H_{13}$ |
| 5 | $C_6F_{13}$ | $C_4H_9$ |
| 6 | $C_6F_{13}$ | $C_{18}H_{37}$ |
| 7 | $C_{10}F_{21}$ | $C_4H_9$ |
| 8 | $C_{10}F_{21}$ | $C_{18}H_{37}$ | where $R_f$ was $C_4F_9$ or $C_{10}F_{21}$, to give fluorochemical aminoalcohol of this invention having the structure $R_f\text{—CH}_2\text{—CH(OH)CH}_2\text{NH—}R_h$, where $R_f$ and $R_h$ are as shown in Table 2. The epoxides can be prepared as described in J. Org. Chem., 26, 2089-2095 (1961)

TABLE 2

Structures of Examples 9-11
$R_f\text{CH}_2\text{—CH(OH)CH}_2\text{NH-}R_H$

| Example | $R_f$ | $R_H$ |
| --- | --- | --- |
| 9 | $C_4F_9$ | $C_{18}H_{37}$ |
| 10 | $C_{10}F_{21}$ | $C_{18}H_{37}$ |
| 11 | $C_{10}F_{21}$ | $C_4H_9$ |

Examples 12-15

Additional aminoalcohols of this invention were prepared as in Example 1 except with different substituted on the sulfonamido nitrogen to give fluorochemical aminoalcohols of this invention having structure $C_4F_9\text{—SO}_2\text{N(R)CH}_2\text{—CH(OH)CH}_2\text{NH—}R_h$, where R and $R_h$ are as shown in Table 3.

TABLE 3

Structures of Examples 12-15
$C_4F_9\text{—SO}_2\text{N(R)CH}_2\text{—CH(OH)CH}_2\text{NH-}R_H$

| Example | R | $R_H$ |
| --- | --- | --- |
| 12 | $C_6H_{13}$ | $C_6H_{13}$ |
| 13 | $C_2H_5$ | $C_{18}H_{37}$ |
| 14 | $C_6H_{13}$ | $C_6H_{13}$ |
| 15 | $C_6H_{13}$ | $C_{18}H_{37}$ |

Example 16

A solution of 37.3 grams potassium hydroxide in 50 mL water was added to 1000 mL dimethylsulfoxide in a two liter three-necked round bottom flask. 226 grams of 2,2,3,3,4,4,5,5,6,6,7,7,8,8,8-pentadecafluoro1-octanol was added in one portion followed by 77.4 grams epibromohydrin. The reaction was stirred at room temperature overnight. The reaction was diluted with excess water and the epoxide

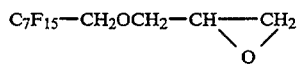

was separated and distilled. This epoxide was then treated with octadecylamine as described in Example 1 to give the fluorochemical aminoalcohol of this invention having the structure $C_7F_{15}\text{—CH}_2\text{OCH}_2\text{—CH(OH)CH}_2\text{NH—}C_{18}H_{37}$.

Example 17-22

Additional aminoalcohols of this invention were prepared by reacting the epoxide described in Example 1 with the appropriately substituted amine using the method described in Example 1. The number of equivalents of fluorochemical epoxide used was equivalent to the number of amino groups present in the amine starting material. The amines used in Examples 17-22 were respectively aniline, m-xylylenediamine, methylenedianiline, 2,4-diaminotoluene, 1,12-diaminododecane and 1,4-diaminocyclohexane. The resulting fluorochemical aminoalcohols of this invention were isolated having the structures shown in Table 4.

TABLE 4

Structures of Examples 17-22
$[C_8F_{17}\text{—SO}_2\text{N(CH}_3)\text{CH}_2\text{—CH(OH)CH}_2\text{NH}]\text{—}_nR$

| Example | n | R |
| --- | --- | --- |
| 17 | 1 | 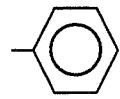 |
| 18 | 2 | 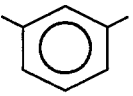 |
| 19 | 2 | 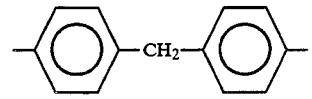 |

TABLE 4-continued

Structures of Examples 17-22
[C$_8$F$_{17}$—SO$_2$N(CH$_3$)CH$_2$—CH(OH)CH$_2$NH]—$_n$R

| Example | n | R |
|---------|---|---|
| 20 | 3 | CH$_3$ 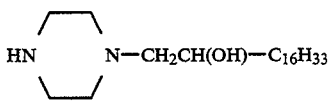 |
| 21 | 2 | —(CH$_2$)$_{12}$— |
| 22 | 2 | 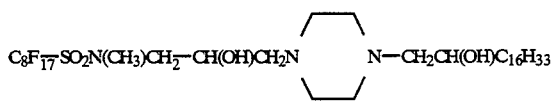 |

Example 23

To a solution of anhydrous piperazine (51.7 g, 600 mmol) in ethanol (200mL) was added 1,2-epoxyoctadecane (40.3 g, 150 mmol) in one portion. The resulting solution was heated to reflux for 22 hours, cooled, and the solvent was removed under reduced pressure. The resulting solid was taken up in chloroform and washed with three portions of warm deionized water, one portion of aqueous saturated sodium chloride solution and dried over anhydrous sodium sulfate. After filtration and solvent removal under reduced pressure, the white to off-white solid (48 g, 90%) amine of structure

HN⟨N—CH$_2$CH(OH)—C$_{16}$H$_{33}$⟩ was isolated.

To a 500 ml round bottom flask was added epoxide A (34.1 g, 60 mmol), the above amine (21.3 g, 60 mmol), and ethanol (60 mL). The resulting solution was heated to reflux for 18 hours, poured into an aluminum foil tin and allowed to solidify with evaporation of the alcoholic solvent to provide a light yellow solid (55.4 g, quantitative recovery) of the fluorochemical aminoalcohol of this invention having structure

C$_8$F$_{17}$SO$_2$N(CH$_3$)CH$_2$—CH(OH)CH$_2$N⟨N—CH$_2$CH(OH)C$_{16}$H$_{33}$⟩

Example 24

To a solution of anhydrous piperazine (86.1 g, 1.0 mole) and triethylamine (25.3 g, 33.3 mL, 250 mmol) in ethanol (250 mL) was added octadecylbromide (83.4 g, 85.4 ml, 250 mmol) in three portions. After stirring overnight at room temperature, chloroform was added to the reaction mixture. The resulting solution was washed with four portions of warm deionized water, one portion of aqueous saturated sodium chloride solution and dried over anhydrous sodium sulfate. After filtration and solvent removal under reduced pressure, an off white solid was isolated. Recrystallization from ethyl acetate afforded (74.4g 88%) purified amine of structure

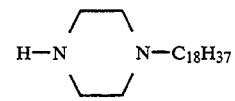

The above amine was treated with epoxide A as in Example 23 to give the fluorochemical aminoalcohol of this invention having structure

C$_8$F$_{17}$—SO$_2$N(CH$_3$)CH$_2$—CH(OH)CH$_2$—N⟨N—C$_{18}$H$_{37}$⟩

Example 25

To a solution of butylamine (43.9 g, 59.3 mL, 600 mmol) in ethanol (100 mL) was added 1,2-epoxyoctadecane (53.7 g, 200 mmol). The resulting mixture was heated to reflux for 2.5 hours, cooled and the alcohol solvent and excess butylamine were removed under reduced pressure to give the resulting off while amine of structure NH(C$_4$H$_9$)—CH$_2$CH(OH)C$_{16}$H$_{33}$.

The above amine was treated with epoxide A as in Example 23 to give the fluorochemical aminoalcohol of this invention having structure C$_8$F$_{17}$—CO$_2$N(CH$_3$)CH$_2$—CH(OH)CH$_2$N(C$_4$H$_9$)—CH$_2$CH(OH)C$_{16}$H$_{33}$.

Comparative Example C1

C$_8$F$_{17}$—C$_{18}$H$_{37}$ was prepared as described in *Macromolecules*, Volume 17, p2786 (1984) by reacting perfluorooctyl iodide with 1-octadecene.

Comparative Example C2

17.7 grams potassium hydroxide was dissolved in 400 mL ethanol in a one liter three-necked round bottom flask. 150.1 grams N-methyl-perfluorodecanesulfonamide was added and the reaction was stirred at room temperature for 30 min. Octadecylbromide (81.6 g) was added and the reaction mixture was heated to 75° C. and stirred overnight. The reaction mixture was then cooled to room temperature and diluted with excess water. The solid product, having structure C$_{10}$F$_{21}$—SO$_2$N(CH$_3$)—C$_{18}$H$_{37}$, was filtered and air dried.

Comparative Example C3

55.7 grams N-hydroxyethyl-N-methyl-perfluorooctanesulfonamide was dissolved in 250 mL ethyl acetate in a one liter three-necked round bottom flask. Next, 29.5 g octadecylisocyanate was added followed by 0.1 g stannous octanoate catalyst. The reaction was heated to reflux and stirred overnight. IR indicated the absence of isocyanate peak. The reaction was cooled to room temperature and solvent was removed under reduced pressure to give product of structure C$_8$F$_{17}$—SO$_2$N(CH$_3$)—CH$_2$CH$_2$OC(O)NHC$_{18}$H$_{37}$.

Comparative Example C4

To a 500 mL round bottom flask was added amide A (102.6 g, 200 mmol), 1,2-epoxyoctadecane (85% purity, 63.2 g, 200 mmol), 4-dimethylaminopyridine (0.61 g, 2.5 mol %) and alcohol (50 mL). The resulting solution was heated to reflux for 21 hours, poured into an aluminum tin and allowed to solidify with evaporation of the alcoholic solvent. The light yellow solid, C$_8$F$_{17}$SO$_2$N $(CH_3)CH_2CH(OH)C_{16}H_{23}$, was isolated with quantitative recovery.

Comparative Example C5

Compound of structure $C_8F_{17}SO_2N(CH_3)CH_2CH(CH_2Cl)OC(O)NHC_{16}H_{33}$ was prepared as in Comparative Example C3 using N-(3-chloro-2-hydroxypropyl)-N-methyl-perfluorooctanesulfonamide in place of the alcohol used there.

The compositions of the above Examples and Comparative Examples were blended with polypropylene, extruded into fiber, and knitted into socks as described above. The amount of the fluoroaliphatic radical-containing composition used was varied to give a theoretical fluorine content of either 1500 or 3000 ppm. The oil-repellency, water-repellency, of each sock was determined as described above. The data shown in Table 5 is the average of the results of from 1 to 5 samples.

TABLE 5

| Composition of Example | Theoretical Fluorine Content (ppm) | OR | WR | Measured fluorine (ppm) |
|---|---|---|---|---|
| 1 | 1500 | 4 | 4 | 1158 |
|   | 3000 | 3 | 4 | 2595 |
| 2 | 1500 | F | 0 | 661 |
|   | 3000 | 1 | 0 | 1302 |
| 3 | 1500 | F | 1 | 1234 |
|   | 3000 | F | 1 | 1810 |
| 4 | 1500 | 1 | F | 1077 |
|   | 3000 | F | 1 | 2087 |
| 5 | 1500 | F | F | 809 |
|   | 3000 | F | F | 1223 |
| 6 | 1500 | 4 | 3 | 1010 |
|   | 3000 | 3 | 3 | 2276 |
| 7 | 1500 | F | F | 950 |
|   | 3000 | F | F | 2568 |
| 8 | 1500 | 3 | 3 | 1178 |
|   | 3000 | 3 | 2 | 2167 |
| 9 | 1500 | F | F | 960 |

TABLE 5-continued

| Composition of Example | Theoretical Fluorine Content (ppm) | OR | WR | Measured fluorine (ppm) |
|---|---|---|---|---|
|   | 2500 | F | 1 | 1983 |
| 10 | 1500 | 5 | 4 | 1198 |
|   | 3000 | 5 | 5 | 2592 |
| 11 | 1500 | F | F | 702 |
|   | 3000 | F | F | 722 |
| 16 | 1500 | F | 0 | 749 |
|   | 3000 | 1 | 2 | 1309 |
| 17 | 1500 | 0 | F | 1408 |
|   | 1300 | 0 | F | 2238 |
| C3 | 1500 | 0 | 1 | — |
|   | 3000 | 0 | 7 | — |
| C4 | 1500 | 1 | 2 | 1139 |
|   | 3000 | 3 | 5 | 2115 |

The data in Table 5 show fluoroaliphatic radical-containing amonoalcohols can be used to impart oil and water repellency to polypropylene.

The compositions of the above Examples and Comparative Examples were mixed with polyproplyene, extruded into fiber, and texturized into carpet samples as described above. The amount of the fluoroaliphatic radical-containing composition used was varied to give a theoretical fluorine content of 1500, 1125, or 3000 ppm. The oil-repellency, water-repellency, and walk-on-soiling rating for each carpet sample was determined as described above. The data reported in Table 6 is the average of from 1 to 5 samples. The OR and WR data are reported for the sample before any walk-on cycles(O), and after the number of cycles shown in Table 6. The OR and WR data are shown in Table 6 as pairs separated by a coma, i.e. an entry in Table 6 of "1,2" means the sample had an average OR of 1 and an average WR of 2. The walk-on-soiling performance is shown after the number of cycles shown in Table 5.

TABLE 6

| Composition of Example | Theoretical Fluorine content (ppm) | OR, WR Number of Cycle | | | | | | Walk-on-Soiling Cycles | | | | |
|---|---|---|---|---|---|---|---|---|---|---|---|---|
| | | 0 | 1 | 2 | 3 | 4 | 5 | 1 | 2 | 3 | 4 | 5 |
| 1 | 1500 | 4,4 | 0,0 | 1,2 | 0,1 | 0,1 | 0,0 | 0 | 0 | 1 | 0 | 0 |
|   | 3000 | 3,4 | 0,0 | 2,3 | 0,1 | 0,0 | 0,0 | 0 | 0 | 3 | 1 | 0 |
| 2 | 1500 | 0,0 | 0,0 | 0,0 | 0,0 | 0,0 | 0,0 | 0 | 0 | 2 | 0 | 1 |
|   | 3000 | 1,0 | 0,0 | 0,0 | 0,0 | 0,0 | 0,0 | 0 | 0 | 2 | 1 | 1 |
| 3 | 1500 | 0,1 | 0,0 | 0,1 | 0,0 | 0,0 | 0,0 | 0 | 0 | 0 | 0 | 0 |
|   | 3000 | 0,1 | 0,0 | 0,1 | 0,0 | 0,0 | 0,0 | 1 | 1 | 1 | 0 | 0 |
| 4 | 1500 | 0,0 | 0,F | — | — | — | — | 2 | 1 | — | — | — |
|   | 3000 | 0,1 | 0,F | — | — | — | — | 2 | 1 | — | — | — |
| 5 | 1500 | 0,F | 0,0 | — | — | — | — | 1 | 2 | — | — | — |
|   | 3000 | 0,F | 0,F | — | — | — | — | 1 | 2 | — | — | — |
| 6 | 1500 | 4,3 | 0,F | — | — | — | — | 1 | 1 | — | — | — |
|   | 3000 | 3,3 | 0,0 | — | — | — | — | 1 | 1 | — | — | — |
| 7 | 1500 | 0,F | 0,0 | — | — | — | — | 3 | 1 | — | — | — |
|   | 3000 | 0,F | 0,F | — | — | — | — | 5 | 3 | — | — | — |
| 8 | 1500 | 3,3 | 0,0 | — | — | — | — | 1 | 1 | — | — | — |
|   | 3000 | 3,2 | 0,0 | — | — | — | — | 0 | 0 | — | — | — |
| 9 | 1500 | 0,0 | 0,0 | 0,0 | 0,F | 0,F | 0,0 | 0 | 1 | 1 | 1 | 1 |
|   | 2500 | 0,1 | 0,F | 0,F | 0,F | — | | 2 | 3 | 2 | 1 | — |
| 10 | 1500 | 5,4 | 0,0 | | | | | 1 | 3 | — | — | — |
|   | 3000 | 5,4 | 0,0 | | | | | 1 | 1 | — | — | — |
| 11 | 1500 | 0,F | 0,0 | — | — | — | — | −1 | 2 | — | — | — |
|   | 3000 | 0,F | 0,F | — | — | — | — | −3 | 0 | — | — | — |
| 12 | 1500 | 0,0 | — | — | — | — | — | — | — | — | — | — |
|   | 3000 | 1,2 | — | — | — | — | — | — | — | — | — | — |
| 13 | 1500 | 0,5 | — | — | — | — | — | 3 | — | — | — | — |
|   | 3000 | 0,5 | — | — | — | — | — | 2 | — | — | — | — |
| 21 | 1500 | 1,F | — | — | — | — | — | 1 | — | — | — | — |
|   | 3000 | 1,0 | — | — | — | — | — | 2 | — | — | — | — |
| C1 | 1500 | 0,F | 0,0 | 0,0 | 0,0 | 0,0 | 0,0 | 0 | 0 | 0 | 0 | 0 |
|   | 3000 | 0,F | 0,0 | 0,F | 0,0 | 0,0 | 0,0 | 0 | 0 | 0 | 0 | 0 |
| C2 | 1500 | 0,F | 0,0 | 0,0 | 0,0 | 0,0 | 0,0 | 0 | 0 | 1 | 0 | 0 |
|   | 3000 | 0,F | 0,0 | 0,0 | 0,0 | 0,0 | 0,0 | 0 | 0 | 1 | 0 | 0 |
| C3 | 1500 | 1,3 | 0,0 | 0,0 | 0,0 | — | — | 1 | 3 | 1 | 1 | 1 |

TABLE 6-continued

| Composition of Example | Theoretical Fluorine content (ppm) | OR, WR Number of Cycle | | | | | | Walk-on-Soiling Cycles | | | | |
|---|---|---|---|---|---|---|---|---|---|---|---|---|
| | | 0 | 1 | 2 | 3 | 4 | 5 | 1 | 2 | 3 | 4 | 5 |
| | 3000 | 3,6 | 1,1 | 1,1 | 1,1 | — | — | 2 | 2 | 2 | 2 | 2 |
| C4 | 1500 | 0,1 | — | — | — | — | — | 0 | — | — | — | — |
| | 3000 | 1,1 | — | — | — | — | — | 0 | — | — | — | — |
| C5 | 1125 | 1,3 | 0,F | 0,F | 0,F | — | — | 1 | 2 | 3 | 2 | — |

The data in Table 6 show the compositions of this invention generally had improved soil resistance compared to a control sample. The control sample, which did not contain a fluorochemical, had a walk-on-soiling value of 0. Particularly effective compositions were those that contained a fluoroaliphatic radical-containing composition that comprised more than 4 fully-fluorinated carbon atoms.

Example 30

113.8 grams epoxide A was dissolved in 100 mL toluene in a 500 mL three-necked round bottom flask equipped with an overhead stirrer, thermometer, addition funnel and electric heating mantle. The temperature of the reaction was raised to 75° C. and 53.9 grams octadecylamine (0.2 mole) was added in portions. The reaction was heated and stirred at 75° C. overnight. 36.0 grams dimethyl carbonate (0.4 mole, 2 equivalents) was slowly added followed by the dropwise addition of 21.6 grams of 25 wt % sodium methoxide in methanol (0.1 mole). A precipitate soon formed after addition of the methoxide was complete. Heating at 75° C. and stirring was continued for six hours. The reaction was then cooled to room temperature diluted with 250 mL deionized water and filtered. The precipitate was allowed to air dry to give the oxazalidinone having structure

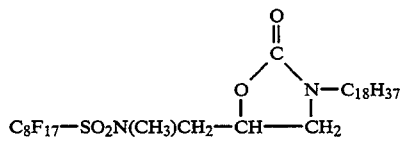

Various modifications and alterations of this invention will become apparent to those skilled in the art without departing from the scope and spirit of this invention.

What is claimed is:

1. A thermoplastic composition comprising fluoroaliphatic radical-containing aminoalcohol and thermoplastic synthetic organic polymer.

2. The composition of claim 1 wherein said fluoroaliphatic radical-containing aminoalcohol comprises a fluoroaliphatic moiety and an organic moiety comprising a secondary aliphatic hydroxyl group and a primary, secondary, or tertiary aliphatic amino group wherein said amino group and hydroxyl group are each bonded to different aliphatic, fully-saturated carbon atoms which are bonded to each other in a hydrocarbon chain wherein said hydroxyl group is located on the hydrocarbon chain proximal to said fluoroaliphatic moiety and said amino group is located on the hydrocarbon chain distal to said fluoroaliphatic moiety.

3. Composition comprising thermoplastic synthetic organic polymer and fluoroaliphatic radical-containing aminoalcohol wherein said fluoroaliphatic radical-containing aminoalcohol is

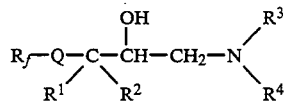

where $R_f$ is a fluorinated, monovalent, saturated aliphatic radical of at least two fully fluorinated carbon atoms; Q is a divalent linking group; $R^1$ and $R^2$ are independently H or an organic radical, $R^1$ and $R^2$ can, together with the carbon atom to which they are bonded, form a cyclic aliphatic ring of 5 to 8 carbon atoms; $R^3$ and $R^4$ are independently H or organic radical, $R^3$ and $R^4$ can, together with the nitrogen atom to which they are bonded, form a heterocyclic nonaromatic ring containing 6 to 8 atoms.

2. The composition of claim 1 wherein said Q is selected from the group consisting of —$(CH_2)_n$— where n is from 0 to 6, —CO—, —CONR—, —$SO_2$NR—, where R is H or lower alkyl, or combinations thereof; said $R_f$ is $C_nF_{2n+1}$ where n is from 5 to 20; $R^1$, $R^2$, and $R^3$ are H; and $R_4$ is $C_yH_{2y+1}$ where y is from 4 to 20.

3. Composition of claim 1 wherein said polymer is polyamide, polyester, polyurethane, or polyolefin.

4. A shaped article comprising the composition of claim 1.

5. Fiber, comprising the composition of claim 1, said fiber being oil and water repellent.

6. Fiber of claim 5 wherein said fibers are blown microfibers.

7. Fibers of claim 5 wherein said fibers are in the form of carpet yarn.

8. Fiber of claim 5 having a fluorine content in the range of about 100 to 10,000 ppm based on the weight of the fiber.

9. Film comprising the composition of claim 1, said fiber being oil and water repellent.

10. Film of claim 9 having a fluorine content in the range of about 100 to 10,000 ppm based on the weight of the fiber.

* * * * *